(12) United States Patent
Shibuya et al.

(10) Patent No.: US 6,806,395 B2
(45) Date of Patent: Oct. 19, 2004

(54) PROCESS FOR PREPARATION OF 3,5-BISALKYLPHENOLS

(75) Inventors: Kimiyuki Shibuya, Saitama (JP); Tadaaki Ohgiya, Saitama (JP); Toru Miura, Tokyo (JP); Kazuhiro Onogi, Saitama (JP)

(73) Assignee: Kowa Co., Ltd., Nagoya (JP)

( * ) Notice: Subject to any disclaimer, the term of this patent is extended or adjusted under 35 U.S.C. 154(b) by 27 days.

(21) Appl. No.: 10/380,169

(22) PCT Filed: Sep. 21, 2001

(86) PCT No.: PCT/JP01/08232

§ 371 (c)(1),
(2), (4) Date: Mar. 18, 2003

(87) PCT Pub. No.: WO02/24618

PCT Pub. Date: Mar. 28, 2002

(65) Prior Publication Data

US 2004/0044255 A1 Mar. 4, 2004

(30) Foreign Application Priority Data

Sep. 21, 2000 (JP) ........................................ 2000-286645
Feb. 28, 2001 (JP) ........................................ 2001-54802

(51) Int. Cl.$^7$ ............................................. C07C 39/06
(52) U.S. Cl. ....................... 568/782; 568/640; 568/648; 568/744; 568/763; 568/764; 568/766; 568/772; 568/799
(58) Field of Search ................................ 568/782, 640, 568/648, 744, 763, 764, 766, 772, 799

(56) References Cited

U.S. PATENT DOCUMENTS

| 2,639,288 | A | * | 5/1953 | Bell et al. .................. 554/7 |
| 2,682,563 | A | * | 6/1954 | Bell et al. .................. 568/766 |
| 2,790,010 | A | | 4/1957 | Shepard |
| 4,163,801 | A | * | 8/1979 | McGarry et al. ............ 514/735 |
| 4,239,918 | A | * | 12/1980 | Keeley ...................... 568/640 |
| 4,460,800 | A | * | 7/1984 | Orlando et al. ............. 568/764 |

FOREIGN PATENT DOCUMENTS

| EP | 1698 | 5/1979 |
| GB | 1296619 | 11/1972 |
| JP | 61-152635 | 7/1986 |

OTHER PUBLICATIONS

D.P. Hsu et al.: "Synthesis and reactions of a zirconocene–benzdiyne equivalent" Tetrahedron Letters, vol. 31, No. 39, pp. 5563–5566 1990.

W.J. Noble et al.: "The effect of pressure on the allylation of hindered phenoxides" J. Org. Chem., vol. 36, No. 1, pp. 193–196 1971.

* cited by examiner

*Primary Examiner*—Michael L. Shippen
(74) *Attorney, Agent, or Firm*—Oblon, Spivak, McClelland, Maier & Neustadt, P.C.

(57) ABSTRACT

A process for producing a 3,5-bisalkylphenol (2) according to the following reaction scheme:

(wherein $R^1$ represents a hydrogen atom, an alkali metal atom, an alkaline earth metal atom, or a hydroxyl-protecting group (other than methyl group); $R^2$ represents a C1 to C5 lower alkyl group or an optionally substituted phenyl group; and each of $R^3$ and $R^4$, which may be identical to or different from each other, represents a lower alkyl group, an aralkyl group, or an aryl group); a carbinol compound (1); and a process for producing the carbinol compound. The production process of the present invention enables efficient and safe production of a variety of 3,5-bisalkylphenols including 3,5-diisopropylphenol, which are important as synthesis intermediates for drugs and agricultural chemicals, in shorter steps at high purity in high yield, thus contributing to consistent supply of drugs and agricultural chemicals.

7 Claims, No Drawings

PROCESS FOR PREPARATION OF 3,5-BISALKYLPHENOLS

TECHNICAL FIELD

The present invention relates to a process for producing 3,5-diisopropylphenol or a similar compound, which serves as an intermediate for producing anti-inflammatory agents, pesticides, etc.; to a carbinol compound for use in production of the phenol compound; and to a process for producing the carbinol compound.

BACKGROUND ART 3,5-Diisopropylphenol is an essential synthesis intermediate for producing, for example, pyridine derivatives (WO 99/24404) serving as anti-inflammatory agents, as well as carbamate derivatives (Japanese Patent Application Laid-Open (kokai) No. 51-112519) serving as pesticides.

Conventionally, 3,5-diisopropylphenol is produced through any of a variety of synthesis processes employing 1,3-diisopropylbenzene as a starting material. Such processes include those represented by the following known synthesis schemes a and b:

(Synthesis scheme a)

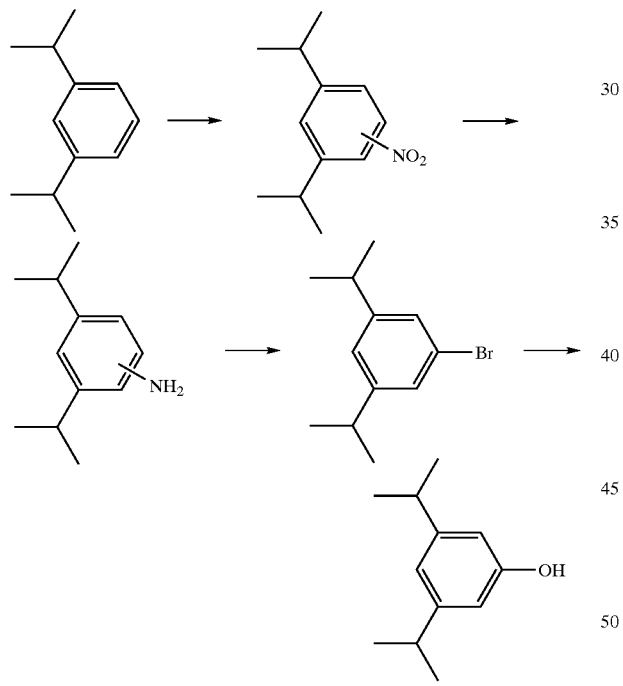

Overall yield: 45%

(Journal of Organic Chemistry Vol. 36, p. 193–196 (1971)) and (Synthesis scheme b)

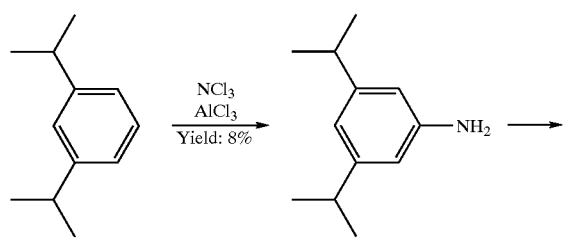

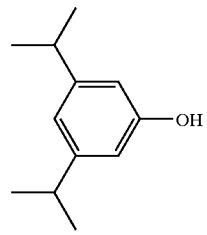

(Journal of Organic Chemistry Vol. 32, p. 585–588 (1967)).

However, syntheses performed through any of these two schemes have drawbacks. For example, when synthesis scheme a is employed, cumbersome purification steps are required and overall yield is low (approximately 45%). Although synthesis scheme b includes only two steps, introduction of an amino group by use of trichloroamine, which is toxic and explosive, performed in the first step raises a problem in terms of safety, and low yield as low as 8% is another problem.

Japanese Patent Application Laid-Open (kokai) No. 61-152635 and U.S. Pat. No. 2,790,010 disclose a two-step process for synthesizing 3,5-diisopropylphenol employing 1,3,5-triisopropylbenzene as a starting material as shown in the following synthesis scheme c.

(Synthesis scheme c)

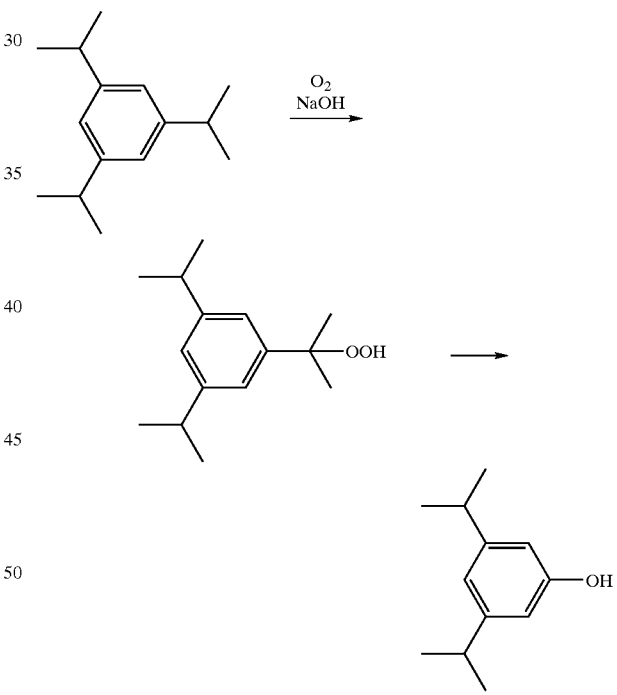

Overall yield: 56%

Although overall yield reaches 56%, synthesis scheme c also has drawbacks such as transformation to a toxic, explosive peroxide intermediate having poor stability and requirement of rectification for yielding a final product. Accordingly, synthesis schemes a to c have been unsuitable for synthesizing 3,5-diisopropylphenol on a large scale.

In addition to synthesis schemes a to c, there have been reported related synthesis methods including alkylation of a phenol species by use of propene (Japanese Patent Application Laid-Open (kokai) Nos. 46-6018 and 54-61131).

However, the methods are not practical, since selectivity and yield are poor, and formed isomers are difficult to separate from one another.

DISCLOSURE OF THE INVENTION

Thus, an object of the present invention is to provide a process for producing 3,5-bisalkylphenol of high purity, which process comprises a small number of steps and attains high production efficiency and yield with high safety.

In view of the foregoing, the present inventors have carried out extensive studies on a process suitable for producing 3,5-bisalkylphenol on a large scale, and have found that 3,5-bisalkylphenol can be produced at high yield through a two-step or three-step process employing a novel carbinol compound as an intermediate which is obtained by alkylating an isophthalate ester derivative. The present invention has been accomplished on the basis of this finding.

Accordingly, the present invention provides a process, as shown in the following reaction scheme:

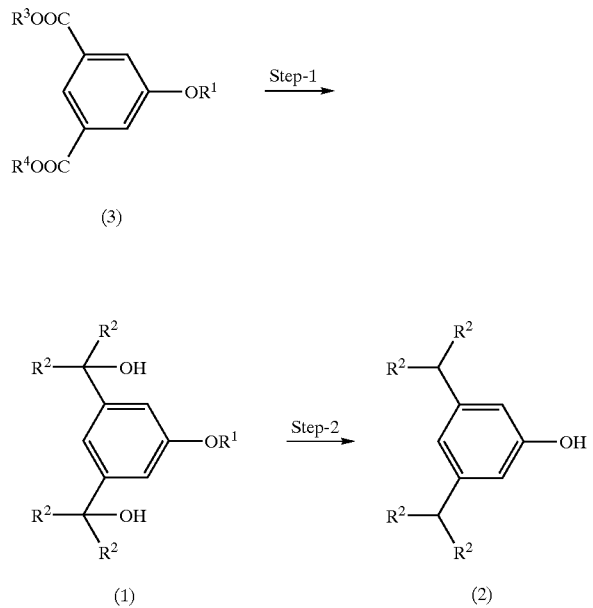

[wherein $R^1$ represents a hydrogen atom, an alkali metal atom, an alkaline earth metal atom, or a hydroxyl-protecting group (other than methyl group); $R^2$ represents a C1 to C5 lower alkyl group or an optionally substituted phenyl group; and each of $R^3$ and $R^4$, which may be identical to or different from each other, represents a lower alkyl group, an aralkyl group, or an aryl group], for producing 3,5-bisalkylphenol (2), characterized by comprising reacting an isophthalate ester derivative represented by formula (3) with a metallic alkylating agent, to thereby form a carbinol compound represented by formula (1) (step-1), and subsequently, hydrogenolyzing the carbinol compound and, in accordance with needs, removing the hydroxyl-protecting group (step-2).

The present invention also provides a carbinol compound represented by formula (1) shown in the above reaction scheme.

The present invention also provides a process for producing 3,5-bisalkylphenol (2) characterized by comprising hydrogenolyzing a carbinol compound represented by formula (1) shown in the above reaction scheme and, in accordance with needs, removing the hydroxyl-protecting group.

The present invention also provides a process for producing a carbinol compound represented by formula (1) characterized by comprising reacting an isophthalate ester derivative represented by formula (3) shown in the above reaction scheme with a metallic alkylating agent.

BEST MODE FOR CARRYING OUT THE INVENTION

In the present invention, examples of preferred alkali metal atoms, represented by $R^1$ in formula (1) or (3), include lithium, sodium, and potassium. Examples of preferred alkaline earth metal atoms include calcium and magnesium.

No particular limitation is imposed on the species of the hydroxyl-protecting group, represented by $R^1$, so long as the group protects hydroxyl group so as to prevent decrease in solubility of the corresponding compound due to formation of a metal salt through reaction of the hydroxyl group with an metallic alkylating agent and the group is caused to leave during hydrogenolysis or through a known method such as acid or alkali treatment.

Examples of groups which leave during hydrogenolysis include benzyl, trityl, benzhydryl, p-methoxybenzyl, benzyloxymethyl, and benzyloxycarbonyl. Examples of groups which do not leave during hydrogenolysis but do leave through acid treatment, alkali treatment, or another treatment include acetal type protecting groups such as methoxymethyl, tetrahydropyranyl, and methoxyethoxymethyl; alkyl groups such as ethyl, n-propyl, isopropyl, n-butyl, sec-butyl, t-butyl, and n-pentyl; alkenyl groups such as allyl; alkynyl groups such as propargyl; aralkyl groups such as 1-phenylethyl, 1-phenylpropyl, and 2-phenylpropyl; silyl groups such as triethylsilyl, t-butyldimethylsilyl, and t-butyldiphenylsilyl; sulfonyl groups such as p-toluenesulfonyl, and methanesulfonyl; acyl groups such as acetyl, benzoyl, propionyl, butyryl, and isobutyryl; carbonate ester groups such as methoxycarbonyl, ethoxycarbonyl, t-butyloxycarbonyl, and trichloroethoxycarbonyl; p-bromophenacyl group; and phenylcarbamoyl group.

Of these, groups which leave during hydrogenolysis are preferably employed, since hydrogenolysis of carbinol hydroxyl group and deprotection of hydroxyl group are simultaneously performed.

$R^2$ represents a C1 to C5 lower alkyl group or an optionally substituted phenyl group. Examples of preferred C1 to C5 lower alkyl groups include methyl, ethyl, n-propyl, isopropyl, n-butyl, and n-pentyl. Of these, methyl and ethyl are more preferred, with methyl being particularly preferred.

Examples of optionally substituted phenyl groups include phenyl groups mono-substituted or di-substituted by a lower alkoxy group, a lower alkyl group, a halogen atom, a lower alkylthio group, or a similar group. Specific examples of optionally substituted phenyl groups include phenyl, methoxyphenyl, ethoxyphenyl, fluorophenyl, chlorophenyl, bromophenyl, iodophenyl, and methylthiophenyl.

Examples of lower alkyl groups, represented by $R^3$ or $R^4$, include C1 to C7 linear or branched alkyl groups. Specific examples include methyl, ethyl, n-propyl, isopropyl, n-butyl, sec-butyl, n-pentyl, isopentyl, n-hexyl, isohexyl, n-heptyl, and isoheptyl. Of these, C1 to C5 alkyl groups are preferred, with methyl being particularly preferred.

Examples of aralkyl groups, represented by $R^3$ and $R^4$, aralkly groups having a C1 to C3 alkyl moiety. Specific examples include phenyl-(C1 to C3) alkyl groups such as benzyl, 1-phenylethyl, 1-phenylpropyl, and 2-phenylpropyl. Of these, benzyl is particularly preferred.

Examples of aryl groups, represented by $R^3$ and $R^4$, include phenyl, naphthyl, and phenyl or naphthyl group having a substituent such as methyl or methoxy.

The steps of the production process according to the present invention will next be described in detail.

Step-1

The carbinol compound (1) can be produced by reacting an isophthalate ester derivative (3) with a metallic alkylating agent.

Examples of the metallic alkylating agent include Grignard reagents such as methylmagnesium bromide, ethylmagnesium bromide, propylmagnesium bromide, isopropylmagnesium bromide, butylmagnesium bromide, pentylmagnesium bromide, phenylmagnesium bromide, methylmagnesium chloride, and methylmagnesium iodide; Grignard reagents prepared from activated magnesium; organometallic reagents such as methyllithium and butyllithium; and organometallic reagents containing a rare earth element (e.g., samarium) such as a reagent prepared from an alkyl halide and samarium iodide. Of these, methylmagnesium bromide is preferred.

Preferably, the metallic alkylating agent is used in an amount of 4 to 8 equivalents based on the isophthalate ester derivative (3).

No particular limitation is imposed on the reaction solvent so long as the solvent can dissolve starting compounds and does not inhibit formation of a target compound. Examples include tetrahydrofuran, diethyl ether, diisopropyl ether, dioxane, 1,2-dimethoxyethane, toluene, and benzene. Of these, tetrahydrofuran is preferred. In addition, a solubilizing aid such as tetramethylethylenediamine or hexamethylphosphoramide is preferably added to the solvent. Furthermore, Lewis acid such as trifluoroboron-diethyl ether complex, titanium tetrachloride, cerium chloride, or trimethylaluminum; and an alkylammonium salt such as tetrabutylammonium bromide may be added to the solvent.

The reaction is performed at 0 to 100° C. in a nitrogen or argon atmosphere for 3 to 10 hours under moisture-free conditions. Particularly, the reaction is preferably performed in tetrahydrofuran for 3 to 6 hours under reflux conditions.

After completion of reaction, acid such as dilute hydrochloric acid or dilute sulfuric acid or an aqueous saturated ammonium chloride solution is added to the reaction mixture, and the mixture is extracted with an organic solvent, to thereby yield a carbinol compound (1).

In Step-1, a ketone compound (4) shown below may be by-produced as an impurity. Such an impurity can be removed by subjecting a crude extract to adsorption treatment by use of sulfonylhydrazine resin.

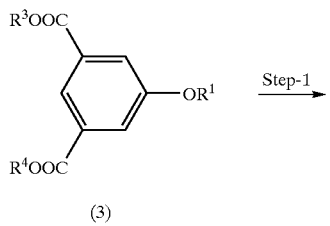

(3)

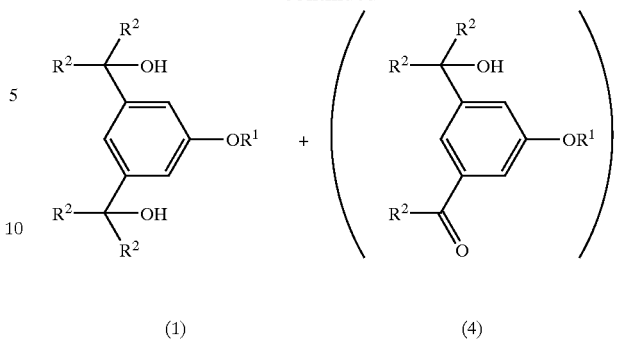

(1)        (4)

Specifically, after completion of alkylation, a crude product is dissolved in an organic solvent such as methanol, 1,2-dichloroethane, 1,2-dimethoxyethane, acetonitrile, or tetrahydrofuran, preferably in methanol, and sulfonylhydrazine resin is added to the resultant solution. The formed ketone compound (4) can be adsorbed by the sulfonylhydrazine resin by shaking the mixture at room temperature to 100° C., preferably at room temperature to 50° C. The thus-obtained reaction mixture is subjected to filtration, to thereby obtain a high-purity carbinol compound (1) from which the ketone compound (4) is removed. The time required for the reaction can be remarkably shortened by adding acetic acid in an amount of 5% (V/V) to the aforementioned solvent such as dichloromethane, 1,2-dichloroethane, 1,2-dimethoxyethane, acetonitrile, or tetrahydrofuran and shaking the mixture at room temperature.

The sulfonylhydrazine resin used in the present invention can be produced by transforming a starting resin (e.g., poly(styrenesulfonic acid) resin) to the corresponding resin. Specifically, a styrenesulfonyl resin prepared from Amberlyst A-15 (product of Rohm & Haas) in accordance with a method described in Journal of Organic Chemistry Vol. 44, p. 4634 (1979)) or a commercially available poly (styrenesulfonylhydrazine) resin (product of Argonaut) is preferably used.

By performing reaction of step-2 after removal of the ketone compound in a manner as described above, 3,5-bisalkylphenol containing no ketone-derived substance can be obtained, leading to enhancement in purity.

Among isophthalate ester derivatives (3) serving as a starting substance, a compound ($R^1$=a hydroxyl-protecting group) can be obtained by protecting, through a routine method, the hydroxyl group of a commercially available 5-hydroxyisophthalate diester derivative.

Step-2

3,5-Bisalkylphenol (2) can be produced by hydrogenolyzing a carbinol compound (1) and, in accordance with need, removing a hydroxyl-protecting group.

Hydrogenolysis of step-2 can be performed through any of customary processes. For example, there can be employed (i) a hydrogenolysis method including dissolving a carbinol compound (1) in an organic solvent such as ethanol, isopropyl alcohol, or n-butanol and adding concentrated hydrochloric acid to the solution in the presence of a catalyst such as palladium-carbon, palladium black, palladium hydroxide, or platinum oxide, preferably in the presence of palladium-carbon at room temperature to refluxing temperature or (ii) the Birch's reduction employing liquid ammonia and sodium.

When $R^1$ is a hydroxyl-protecting group which can leave during hydrogenolysis; e.g., benzyl, trityl, benzhydryl, p-methoxybenzyl, benzyloxymethyl, or benzyloxycarbonyl, the protecting group is removed during hydrogenolysis, to thereby form a 3,5-bisalkylphenol (2). When a hydroxyl-protecting group which is difficult to leave during the aforementioned hydrogenolysis is employed, deprotection is performed through acid treatment, alkali treatment, or other known means after performance of hydrogenolysis.

The acid treatment or alkali treatment is performed, for example, in an alcoholic solvent such as methanol, ethanol, or butanol; a mixture of water and the alcoholic solvent; or a mixture of water and tetrahydrofuran, dioxian, or a similar solvent. Examples of acids employed in the acid treatment include inorganic acids such as hydrochloric acid, sulfuric acid, phosphoric acid, hydrobromic acid, and hydroiodic acid; organic sulfonic acids such as methanesulfonic acid and p-toluenesulfonic acid; and organic carboxylic acids such as acetic acid and oxalic acid. Examples of alkali compounds used in the alkali treatment include alkali metal hydroxides such as sodium hydroxide and potassium hydroxide; alkali metal carbonates such as sodium carbonate and potassium carbonate; metal alkoxides such as sodium methoxide and sodium ethoxide; and organic bases such as piperidine and morpholine. In addition to acid treatment or alkali treatment, treatment with Lewis acid such as aluminum trichloride or boron tribromide may be employed.

The target compound can be isolated through a purification method generally employed in the field of organic synthesis; e.g., filtration, washing, drying, recrystallization, and a variety of chromatographic methods.

EXAMPLES

The present invention will next be described in more detail by way of examples.

Referential Example 1

Synthesis of Dimethyl 5-benzyloxyisophthalate

To a solution of dimethyl 5-hydroxyisophthalate (50.0 g, 238 mmol) in N,N-dimethylformamide (500 mL), benzyl bromide (29.5 mL, 248 mmol) was added dropwise in the presence of potassium carbonate (42.4 g, 307 mmol), and the reaction mixture was stirred for 2 hours at room temperature, followed by addition of water thereto. The resultant mixture was extracted with diethyl ether. The resultant organic layer was washed sequentially with water and saturated brine and dried over sodium sulfate anhydrate. The solvent was removed under reduced pressure, to thereby yield a solid. The solid was crystallized from diethyl ether, to thereby yield 68.9 g of dimethyl 5-benzyloxyisophthalate as colorless needles (yield 96%).

Melting point: 96–97° C. IR(KBr)cm$^{-1}$: 3420, 2955, 1721, 1596, 1501, 1460. $^1$H-NMR (CDCl$_3$)δ: 3.94(6H,s), 5.15(2H,s), 7.33–7.46(5H,m), 7.84(2H,s), 8.30(1H,s). EIMS m/z: 300(M$^+$), 91(100) Elementary analysis: as C$_{17}$H$_{16}$O$_5$ Calculated: C, 67.99; H, 5.37. Found: C, 68.01; H, 5.48.

Example 1

Synthesis of 5-benzyloxy-α,α,α',α'-tetramethyl-1,3-benzenedimethanol

Under argon atmosphere, dimethyl 5-benzyloxyisophthalate (28.6 g, 95.2 mmol) was dissolved in anhydrous tetrahydrofuran (THF) (100 mL), and a 12% (W/V) solution (520 mL) of methylmagnesium bromide (523.3 mmol) in anhydrous THF was added dropwise to the solution under ice-cooling. The mixture was refluxed for 3 hours. After cooling the reaction mixture, methanol, water, and 1N HCl were added to the reaction mixture, and the resultant mixture was extracted with chloroform. The resultant organic layer was washed sequentially with water and saturated brine and dried over sodium sulfate anhydrate. The solvent was removed under reduced pressure, to thereby yield a solid residue.

The thus-obtained residue was dissolved in methanol (1,200 mL), and poly(styrenesulfonylhydrazine) resin (37.3 g, 100.3 mmol) was added to the solution. The resultant mixture was shaken at room temperature for 36 hours. The reaction mixture was subjected to filtration, and the filtrate was concentrated under reduced pressure, to thereby yield crystals. The crystals were recrystallized from hexane-chloroform, to thereby yield 26.6 g of 5-benzyloxy-α,α,α',α'-tetramethyl-1,3-benzenedimethanol as colorless needles (yield 93%), Melting point: 146–147° C. IR(KBr)cm$^{-1}$: 3474, 3267, 2976, 1592, 1429, 1364. $^1$H-NMR(CDCl$_3$)δ: 1.58(12H,s), 5.08(2H,s), 7.02(2H,s), 7.22(1H,s), 7.33(1H,t,J=7.0 Hz), 7.39(2H,t,J=7.0 Hz), 7.45(2H,d,J=7.0 Hz). EIMS m/z: 300 (M$^+$), 91(100) Elementary analysis: as C$_{19}$H$_{24}$O$_3$ Calculated: C, 75.97; H, 8.05. Found: C, 75.92; H, 8.04.

Example 2

Synthesis of 3,5-diisopropylphenol

To a solution of 5-benzyloxy-α,α,α',α'-tetramethyl-1,3-benzenedimethanol (22.9 g, 76 mmol) in ethanol (500 mL), concentrated hydrochloric acid (2.6 mL) and a 10% palladium-carbon catalyst (8.0 g) were added. Under hydrogen atmosphere, the mixture was stirred for 23 hours at 60° C. The reaction mixture was subjected to filtration, and the filtrate was concentrated under reduced pressure, to thereby yield 13.6 g of 3,5-diisopropylphenol as a solid (yield 100%). The solid was crystallized from hexane, to thereby yield colorless needles.

Melting point: 51–52° C. IR(KBr)cm$^{-1}$: 3307, 2961, 2926, 2869, 1618, 1595. $^1$H-NMR(CDCl$_3$)δ: 1.22(12H,d,J= 7.0 Hz), 2.83(2H,sept,J=7. Hz), 6.53(2H,s), 6.67(1H,s) EIMS m/z: 178(M$^+$), 163(100)

Example 3

Synthesis of 5-hydroxy-α,α,α',α'-tetramethyl-1,3-benzenedimethanol

Under argon atomosphere, a 12% (W/V) solution (969 mL) of methylmagnesium bromide (975.0 mmol) in anhydrous THF was added dropwise to a solution of dimethyl 5-hydroxyisophthalate (31.5 g, 150.0 mmol) in anhydrous THF (1,500 mL) under ice-cooling. After addition was complete, the reaction mixture was refluxed for 3 hours. After cooling the mixture, an aqueous saturated ammonium chloride solution was added to the reaction mixture, to thereby deactivate the residual Grignard reagent. Subsequently, water and 1N HCl were sequentially added for dilution, followed by extraction with ethyl acetate. The resultant organic layer was washed sequentially with water and saturated brine and dried over sodium sulfate. The solvent was removed under reduced pressure, to thereby yield a solid residue. The thus-obtained residue was dissolved in methanol (1,500 mL), and poly (styrenesulfonylhydrazine) resin (90.3 g, 285.3 mmol) was added to the solution. The resultant mixture was shaken for 24 hours at room temperature, and the resin was removed through filtration. The filtrate and methanol used for washing were combined, and the combined liquid was concentrated under reduced pressure, to thereby yield a white solid. The thus-obtained solid was crystallized from hexane-diethyl ether, to thereby yield 20.6 g of 5-hydroxy-α,α,α',α'-tetramethyl-1,3-benzenedimethanol as colorless needles (yield 65.3%).

Melting point: 137–138° C.

IR(KBr)cm$^{-1}$: 3358, 3227, 2973, 1606, 1503, 1432. $^1$H-NMR(CDCl$_3$)δ: 1.57(12H,s), 6.88(2H,s), 7.15(1H,s). EIMS m/z: 210(M$^+$), 177(100) Elementary analysis: as C$_{12}$H$_{18}$O$_3$ Calculated: C, 68.55; H, 8.63. Found: C, 68.40; H, 8.52.

Example 4

Synthesis of 3,5-diisopropylphenol

To a solution of 5-hydroxy-α,α,α',α'-tetramethyl-1,3-benzenedimethanol (20.0 g, 95.1 mmol) in ethanol (600 mL), concentrated hydrochloric acid (12.0 mL) and a 10% palladium-carbon catalyst (11.0 g) were added, and the mixture was stirred under hydrogen atmosphere for 22 hours at room temperature. The reaction mixture was subjected to filtration, and the filtrate was concentrated under reduced pressure, to thereby yield a white solid. The thus-obtained solid was crystallized from hexane, to thereby yield 16.5 g of 3,5-diisopropylphenol as colorless needles (yield 97.3%).

Melting point: 51–52° C. IR(KBr)cm$^{-1}$: 3307, 2961, 2926, 2869, 1618, 1595 $^1$H-NMR(CDCl$_3$)δ: 1.22(12H,d,J=7.0 Hz), 2.83(2H,sept,J=7.0 Hz), 6.53(2H,s), 6.67(1H,s). EIMS m/z: 178(M$^+$) 163(100)

Example 5

Synthesis of 5-benzyloxy-α,α,α',α'-tetraethyl-1,3-benzenedimethanol

The procedure (including reaction and treatment) of Example 1 was repeated, except that methylmagnesium bromide was replaced by ethylmagnesium bromide, to thereby obtain the above-described target as a pale yellow oil.

IR(film)cm$^{-1}$: 3474, 2969, 2937, 2879, 1593, 1498. $^1$H-NMR(CDCl$_3$)δ: 0.74(12H,t,J=7.4 Hz), 1.78(4H,dq,J=14.3, 7.4 Hz), 1.85(4H,dq,J=14.3,7.4 Hz), 5.07(2H,s), 6.90 (2H,s), 6.92(1H,s), 7.31(1H,t,J=7.2 Hz), 7.38(2H,t,J=7.2 Hz), 7.45(2H,d,J=7.2 Hz).

Example 6

Synthesis of 3,5-bis(1-ethylpropyl)phenol

The procedure (including reaction and treatment) of Example 2 was repeated, except that 5-benzyloxy-α,α,α',α'tetramethyl-1,3-benzenedimethanol was replaced by 5-benzyloxy-α,α,α',α'-tetraethyl-1,3-benzenedimethanol, to thereby yield the above-described target as colorless needles.

IR(KBr)cm$^{-1}$: 3350, 2962, 2924, 2872, 1618, 1597. $^1$H-NMR(CDCl$_3$)δ: 0.76(12H,t,J=7.4 Hz), 1.44–1.56(4H, m), 1.58–1.70(4H,m),2.22(2H,t,J=9.2,5.3 Hz), 4.52(1H,s), 6.43(2H,s), 6.48(1H,s).

Example 7

Synthesis of 5-benzyloxy-α,α,α',α'-tetrapropyl-1,3-benzenedimethanol

The procedure (including reaction and treatment) of Example 1 was repeated, except that methylmagnesium bromide was replaced by n-propylmagnesium bromide, to thereby yield the above-described target as a pale yellow oil.

IR(film)cm$^{-1}$: 3470, 2958, 2934, 2872, 1593, 1498 . $^1$H-NMR(CDCl$_3$)δ: 0.84(12H,t,J=7.3 Hz), 0.99–1.11(4H, m), 1.21–1.34(4H,m), 1.72(4H,dt,J=14.1,5.1 Hz), 1.78(4H, dt,J=14.1,5.1 Hz), 5.07(2H,s),6.88(2H,s),6.92(1H,s), 7.32 (1H,t,J=7.2 Hz), 7.38(2H,t,J=7.2 Hz),7.45(2H,d,J=7.2 Hz).

Example 8

Synthesis of 3,5-bis(1-propylbutyl)phenol

The procedure (including reaction and treatment) of Example 2 was repeated, except that 5-benzyloxy-α,α,α',α'-tetramethyl-1,3-benzenedimethanol was replaced by 5benzyloxy-α,α,α',α'-tetrapropyl-1,3-benzenedimethanol, to thereby yield the above-described target as a pale yellow oil. IR(film)cm$^{-1}$: 3348, 2957, 2929, 1617, 1595, 1502. $^1$H-NMR(CDCl$_3$)δ: 0.83(12H,t,J=7.3 Hz), 1.08–1.22(8H, m), 1.41–1.60(8H,m), 2.42(2H,t,J=9.4,5.7 Hz), 4.59(1H, br.s), 6.42(2H,s), 6.48(1H,s).

Example 9

Synthesis of 5-benzyloxy-α,α,α'α'-tetrabutyl-1,3-benzenedimethanol

The procedure (including reaction and treatment) of Example 1 was repeated, except that methylmagnesium bromide was replaced by n-butylmagnesium bromide, to thereby yield the above-described target as colorless powdery crystals.

IR(KBr)cm$^{-1}$: 3466, 2957, 2933, 1609, 1594, 1499. $^1$H-NMR(CDCl$_3$)δ: 0.82(12H,t,J=7.2 Hz), 0.92–1.07(4H, m), 1.13–1.32(12H,m), 1.68–1.86(8H,m), 5.08(2H,s), 6.89 (1H,s), 6.90(2H,s), 7.31(1H,t,J=7.2 Hz), 7.38(2H,t,J=7.2 Hz), 7.45(2H,d,J=7.2 Hz).

Example 10

Synthesis of 3,5-bis(1-butylpentyl)phenol

The procedure (including reaction and treatment) of Example 2 was repeated, except that 5-benzyloxy-α,α,α',α'-tetramethyl-1,3-benzenedimethanol was replaced by 5-benzyloxy-α,α,a',a'-tetrabutyl-1,3-benzenedimethanol, to thereby yield the above-described target as colorless needles. IR(film)cm$^{-1}$: 3355, 2957, 2927, 1616, 1597. $^1$H-NMR(CDCl$_3$)δ: 0.81(12H,t,J=7.3 Hz), 1.05–1.33(16H, m), 1.43–1.63(8H,m), 2.37(2H,t,J=9.1,5.1 Hz), 4.52(1H,s), 6.42(2H,s), 6.47 (1H,s).

Example 11

Synthesis of 5-benzyloxy-α,α,α',α'-tetraisopropyl-1, 3-benzenedimethanol

The procedure (including reaction and treatment) of Example 1 was repeated, except that methylmagnesium bromide was replaced by isopropylmagnesium bromide, to thereby yield the above-described target as a colorless oil. IR(film)cm$^{-1}$: 3536, 2968, 2936, 1591, 1498. $^1$H-NMR (CDCl$_3$)δ: 0.76(12H,d,J=6.8 Hz), 0.83(12H,d,J=6.8 Hz), 2.26(4H,sept,J=6.8 Hz), 5.08(2H,s), 6.91(1H,s), 6.94(2H,s), 7.30(1H,t,J=7.3 Hz), 7.37(2H,t,J=7.3 Hz), 7.45(2H,d,J=7.3 Hz).

Example 12

Synthesis of 3,5-Bis(1-isopropyl-2-menthylpropyl)phenol

The procedure (including reaction and treatment) of Example 2 was repeated, except that 5-benzyloxy-α,α,α', α'-tetramethyl-1,3-benzenedimethanol was replaced by 5-benzyloxy-(α,α,α',α'-tetraisopropyl-1,3-benzenedimethanol, to thereby yield the above-described target as a colorless oil. IR(film)cm$^{-1}$: 3385, 2958, 2928, 1614, 1593, 1489. $^1$H-NMR(CD$_3$OD)δ: 0.66(12H,d,J=6.6 Hz), 0.76(12H,d,J=6.6 Hz), 1.88(2H,t,J=6.6 Hz), 1.99(4H, oct,J=6.6 Hz), 6.23(1H,s), 6.29(2H,s).

Example 13

Synthesis of 5-benzyloxy-α,α,α',α'-tetraphenyl-1,3-benzenedimethanol

The procedure (including reaction and treatment) of Example 1 was repeated, except that methylmagnesium bromide was replaced by phenylmagnesium bromide, to thereby yield the above-described target as a colorless oil.

IR(film)cm$^{-1}$: 3558, 3467, 3061, 3032, 1593, 1492. $^1$H-NMR(CDCl$_3$)δ: 2.72(2H,br.s), 4.87(2H,s), 6.82(1H,s), 6.85(2H,s), 7.17–7.33(25H,m).

Example 14

Synthesis of 3,5-dibenzhydrylphenol

The procedure (including reaction and treatment) of Example 2 was repeated, except that 5-benzyloxy-α,α,α', α'-tetramethyl-1,3-benzenedimethanol was replaced by 5benzyloxy-α,α, α',α'-tetraphenyl-1,3-benzenedimethanol, to thereby yield the above-described target as a colorless oil. IR(film)cm$^{-1}$: 3536, 3410, 3061, 3026, 1597, 1494. $^1$H-NMR(CDCl$_3$)δ: 4.52(1H,br.s), 5.40(2H,s), 6.37(2H,s), 6.57(1H,s), 7.05(8H,dd,J=8.3,1.5 Hz), 7.15–7.26(12H,m).

Industrial Applicability

The production process of the present invention enables efficient and safe production of a variety of 3,5-bisalkylphenols including 3,5-diisopropylphenol, which are important as synthesis intermediates for drugs and agricultural chemicals, in shorter steps at high purity in high yield, thus contributing to consistent supply of drugs and agricultural chemicals.

What is claimed is:

1. A carbinol compound represented by the following formula (1):

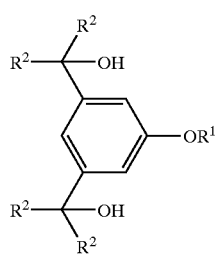

(1)

(wherein $R^1$ represents a hydrogen atom, an alkali metal atom, an alkaline earth metal atom, or a hydroxyl-protecting group (other than methyl group); and $R^2$ represents a C1 to C5 lower alkyl group or an optionally substituted phenyl group).

2. A process for producing a 3,5-bisalkylphenol represented by the following formula (2):

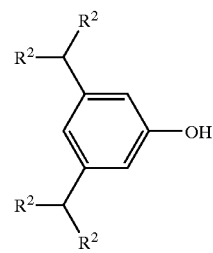

(2)

(wherein $R^2$ represents a C1 to C5 lower alkyl group or an optionally substituted phenyl group) characterized by comprising hydrogenolyzing a carbinol compound represented by the following formula (1):

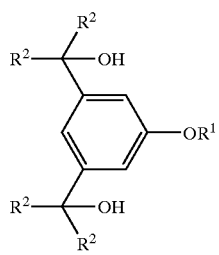

(1)

(wherein $R^1$ represents a hydrogen atom, an alkali metal atom, an alkaline earth metal atom, or a hydroxyl-protecting group (other than methyl group); and $R^2$ has the same meaning as described above) and, in accordance with needs, removing the hydroxyl-protecting group.

3. A process for producing a carbinol compound represented by the following formula (1):

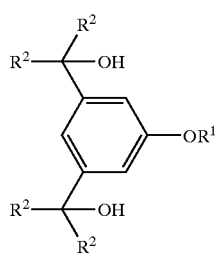

(1)

(wherein $R^1$ represents a hydrogen atom, an alkali metal atom, an alkaline earth metal atom, or a hydroxyl-protecting group (other than methyl group); and $R^2$ represents a C1 to C5 lower alkyl group or an optionally substituted phenyl group) characterized by comprising reacting a metallic alkylating agent with an isophthalate ester derivative represented by the following formula (3):

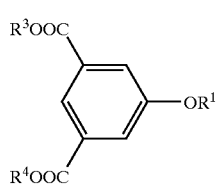

(3)

(wherein $R^1$ has the same meaning as described above; and each of $R^3$ and $R^4$, which may be identical to or different from each other, represents a lower alkyl group, an aralkyl group, or an aryl group).

4. A process for producing a carbinol compound as described in claim 3, which further includes a treatment of adsorbing a by-product by use of a sulfonylhydrazine resin.

5. A process for producing a 3,5-bisalkylphenol represented by the following formula (2):

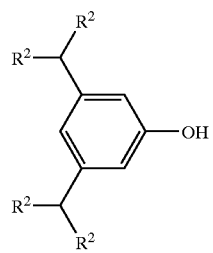

(2)

(wherein $R^2$ represents a C1 to C5 lower alkyl group or an optionally substituted phenyl group) characterized by comprising reacting a metallic alkylating agent with an isophthalate ester derivative represented by the following formula (3):

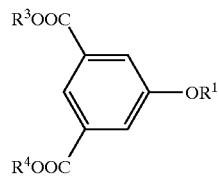

(3)

(wherein $R^1$ represents a hydrogen atom, an alkali metal atom, an alkaline earth metal atom, or a hydroxyl-protecting group (other than methyl group); and each of $R^3$ and $R^4$, which may be identical to or different from each other, represents a lower alkyl group, an aralkyl group, or an aryl group), to thereby form a carbinol compound represented by the following formula (1):

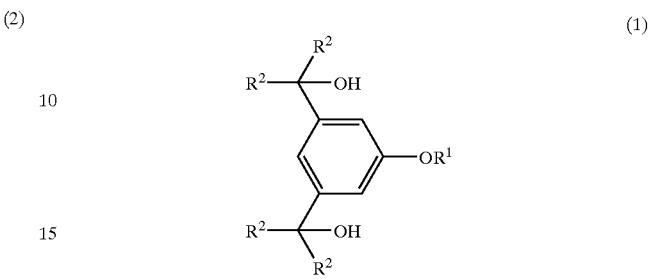

(1)

(wherein each of $R^1$ and $R^2$ has the same meaning as described above) (step-1), and subsequently, hydrogenolyzing the carbinol compound and, in accordance with needs, removing the hydroxyl-protecting group (step-2).

6. A process for producing a 3,5-bisalkylphenol as described in claim 5, wherein the step-1 includes a treatment of adsorbing a by-product by use of a sulfonylhydrazine resin.

7. A process for producing a 3,5-bisalkylphenol as described in any one of claims 2, 5, and 6, wherein $R^2$ in formula (1) or (2) is a methyl group.

* * * * *